United States Patent
Grincourt et al.

(10) Patent No.: US 8,002,957 B2
(45) Date of Patent: Aug. 23, 2011

(54) SENSOR APPARATUS FOR MEASURING AND DETECTING ACETYLENE AND HYDROGEN DISSOLVED IN A FLUID

(75) Inventors: Yves Grincourt, Ottawa (CA); Elena Babes-Dornea, Pierrefonds (CA)

(73) Assignee: General Electric Company, Schenectady, NY (US)

( * ) Notice: Subject to any disclaimer, the term of this patent is extended or adjusted under 35 U.S.C. 154(b) by 904 days.

(21) Appl. No.: 11/968,385

(22) Filed: Jan. 2, 2008

(65) Prior Publication Data

US 2009/0166197 A1    Jul. 2, 2009

(51) Int. Cl.
*G01N 27/27* (2006.01)

(52) U.S. Cl. ......... 204/432; 429/430; 204/431; 204/414

(58) Field of Classification Search ............. 204/400, 204/415, 421–429, 432, 414; 205/781, 782, 205/783.5, 784.5; 73/114.71, 114.72, 114.73; 429/12, 430
See application file for complete search history.

(56) References Cited

U.S. PATENT DOCUMENTS

| | | | |
|---|---|---|---|
| 4,112,737 A | 9/1978 | Morgan | |
| 4,271,474 A | 6/1981 | Belanger et al. | |
| 4,293,399 A | 10/1981 | Belanger et al. | |
| 5,070,738 A | 12/1991 | Morgan | |
| 5,271,263 A | 12/1993 | Gibeault | |
| 5,298,146 A * | 3/1994 | Braden et al. | 204/406 |
| 5,738,773 A | 4/1998 | Criddle et al. | |
| 5,932,079 A * | 8/1999 | Haupt et al. | 204/415 |
| 6,202,473 B1 | 3/2001 | Stokes et al. | |
| 6,324,891 B1 | 12/2001 | Gibeault et al. | |
| 6,436,257 B1 | 8/2002 | Babas-Dornea | |
| 6,446,027 B1 | 9/2002 | O'Keeffe et al. | |
| 6,494,617 B1 | 12/2002 | Stokes et al. | |
| 6,506,296 B2 | 1/2003 | Babes-Dornea et al. | |
| 6,526,805 B1 | 3/2003 | Babes-Dornea et al. | |
| 6,656,335 B2 | 12/2003 | Babes-Dornea et al. | |
| 7,254,986 B2 | 8/2007 | Stokes et al. | |
| 2004/0112764 A1* | 6/2004 | Stokes et al. | 205/782 |
| 2005/0145493 A1* | 7/2005 | Saffell et al. | 204/431 |
| 2006/0032742 A1* | 2/2006 | Babes-Dornea et al. | 204/400 |

* cited by examiner

*Primary Examiner* — Kaj K Olsen
*Assistant Examiner* — Kourtney R Salzman
(74) *Attorney, Agent, or Firm* — James W. Pemrick; Ernest G. Cusick; Frank A. Landgraff

(57) ABSTRACT

A fuel cell sensor is provided for detecting the presence of acetylene and hydrogen in a fluid. The sensor includes a sensing element having first and second gas diffusing electrodes spaced from one another. The first gas diffusing electrode can be used for sensing acetylene. The second gas diffusing electrode can be used for sensing hydrogen. A fuel cell spacer having an acidic electrolyte is disposed between the sensing element and a common electrode. The sensing element can be configured to have a specific ratio of the area between the first gas diffusing electrode in relation to the area of the second gas diffusing electrode.

18 Claims, 7 Drawing Sheets

SENSOR APPARATUS FOR MEASURING AND DETECTING ACETYLENE AND HYDROGEN DISSOLVED IN A FLUID

BACKGROUND OF THE INVENTION

The present invention relates generally to a sensor apparatus for monitoring the presence of acetylene and hydrogen in a fluid such as, for example, an insulating fluid. More specifically, the invention relates to a sensor apparatus in which the concentration of acetylene and hydrogen dissolved in a fluid are determined by the measure of an electric current generated by electrochemical oxidation of the acetylene and hydrogen at detection electrodes.

The following will deal, by way of example only, with the detection of constituents in a fluid that may be an insulating or dielectric fluid. Electrical systems are well known in the art which use an insulating fluid as an insulating substance; these systems include for example transformers, circuit breakers and the like.

It is known that, in the event of a disturbance or malfunction of an above mentioned type of device or system, the result may be the production of one or more gases in the insulating fluid; this may occur for example if a device is working at high temperature or high conditions of electrical stress therein. Such conditions may also produce undesired moisture and/or one or more breakdown products of the dielectric material of the insulating system (i.e. insulating fluid). If such abnormal conditions are allowed to continue uncorrected, this may lead to irreparable damage to the electrical system. A timely (e.g. more or less immediate) detection and/or diagnosis of any such abnormal operation of an electrical apparatus is thus advantageous in order to be able to avoid irreparable harm to such a system.

Accordingly, various monitoring devices and systems have been proposed for the detection of any incipient failure conditions such as for example any undesired increase of the concentration of a fault gas (e.g. a combustible gas such as for example, hydrogen gas ($H_2$), carbon monoxide gas (CO), methane gas ($CH_4$), ethane gas ($C_2H_6$), ethylene gas ($C_2H_4$), acetylene gas ($C_2H_2$) and the like or a non-combustible gas such as for example, carbon dioxide ($CO_2$), moisture (e.g. water or $H_2O$), a breakdown product, contaminant substance, and/or the like contained (e.g. dissolved) in the insulating fluid.

Some such detection and/or monitoring systems are, for example, described in U.S. Pat. No. 4,112,737 (Morgan), U.S. Pat. No. 4,293,399 (Belanger et al), U.S. Pat. No. 4,271,474 (Belanger et al), U.S. Pat. No. 5,070,738 (Morgan), U.S. Pat. No. 5,271,263 (Gibeault) and U.S. Pat. No. 5,738,773 (Criddle et al.).

U.S. Pat. No. 5,738,773 for example illustrates a fuel cell arrangement for detecting oxidizable components of a gas or vapor. The fuel cell comprises first electrode means and second counter electrode means which are connected by an acidic electrolyte. The electrochemical oxidation of a fuel component in the gas results in the formation of a potential difference between the first and second electrode means; the resultant current and/or potential difference can be detected and associated with the presence and/or concentration of combustible gas detected thereby.

U.S. Pat. No. 4,293,399, for example, describes how the concentration of gaseous hydrogen dissolved in a fluid may be determined by a measure of an electric current generated by electrochemical oxidation of the gaseous hydrogen at an electrode of the detector; i.e. by a measure of a current generated in response to the presence of hydrogen (in a gas). The prior art detecting and measuring means described in this U.S. patent comprises a polymeric membrane permeable to hydrogen gas for contact with a fluid containing dissolved hydrogen gas; an electrolyte capable of facilitating oxidation of the hydrogen gas diffused through the polymeric membrane at a first electrode and reduction of an oxygen-containing gas such as air at a second electrode; and a measuring device connected to the fuel cell for measuring the intensity of the electrical current generated by the electrochemical reaction of oxidation of the hydrogen gas, this intensity being proportional to the concentration of hydrogen in the fluid.

It is advantageous for such monitoring (e.g. detection) devices, as described above, to be able to provide an accurate as possible detection and/or diagnosis of the incorrect operation of systems such as, for example, transformers, circuit breakers, shunt reactors or any electro-apparatuses using a dielectric fluid as an insulating substance such as a dielectric liquid (e.g. a dielectric oil) or a dielectric gas (e.g. $SF_6$ gas).

A number of the above mentioned prior art monitoring devices or systems may be limited in that the sample gas received by the detector may be a mixture containing multiple gases, having a relatively low concentration of a target gas which it is desired to detect or monitor; e.g. a low concentration of acetylene gas relative to hydrogen gas. In such case, the low concentration of a target gas relative to the other gases present in a sample gas may be such that one or more of the other gases may interfere with the measurement of a predetermined target gas(es). In other words, the precision of the results of the detecting or monitoring device may thus be less than is desired; i.e. due to that fact that one or more extraneous gases may interfere with the reading of the target gas (e.g. acetylene). Another limitation of the prior art devices is that only one gas can be detected.

The presence, concentration and evolution of even very low concentrations of acetylene and hydrogen dissolved in a dielectric fluid, such as for example a dielectric oil, is a particularly useful indicator of the processes occurring (e.g. default gas production) in the insulated electrical equipment. As mentioned, in addition to acetylene and hydrogen, the dielectric fluid may contain other dissolved gases, such as carbon monoxide, ethylene, ethane, methane, etc. A reliable analysis of acetylene and hydrogen thus requires a detector having an enhanced selectivity for acetylene at very low concentrations in the presence of other such dissolved gases (e.g. hydrogen).

Accordingly, it would be advantageous to have a detector for the specific detection, measuring and monitoring of acetylene and hydrogen dissolved in a dielectric fluid (e.g., a dielectric oil used in a transformer).

BRIEF SUMMARY OF THE INVENTION

The present invention, in accordance with one aspect, provides a fuel cell sensor for detecting the presence of acetylene and hydrogen in a fluid. The sensor includes a sensing element having first and second gas diffusing electrodes spaced from one another. The first gas diffusing electrode can be used for sensing acetylene. The second gas diffusing electrode can be used for sensing hydrogen. A fuel cell spacer having an acidic electrolyte is disposed between the sensing element and a common electrode. The sensing element can be configured to have a specific ratio of the area between the first gas diffusing electrode in relation to the area of the second gas diffusing electrode.

In accordance with another aspect, the present invention provides a fuel cell sensor for detecting the presence of acetylene and hydrogen in a fluid. The sensor includes at least one first sensing element for sensing acetylene, and at least one second sensing element for sensing hydrogen. A fuel cell spacer having an acidic electrolyte is disposed between both the first and second sensing elements and the common electrode.

The present invention, in accordance with yet another aspect, provides an electrochemical sensing element having a plurality of sensing electrodes and a common electrode. The electrochemical sensing element can be used for the simultaneous measurement or quantification of a plurality of different gases dissolved in a fluid.

DETAILED DESCRIPTION OF THE INVENTION

Figure 1:
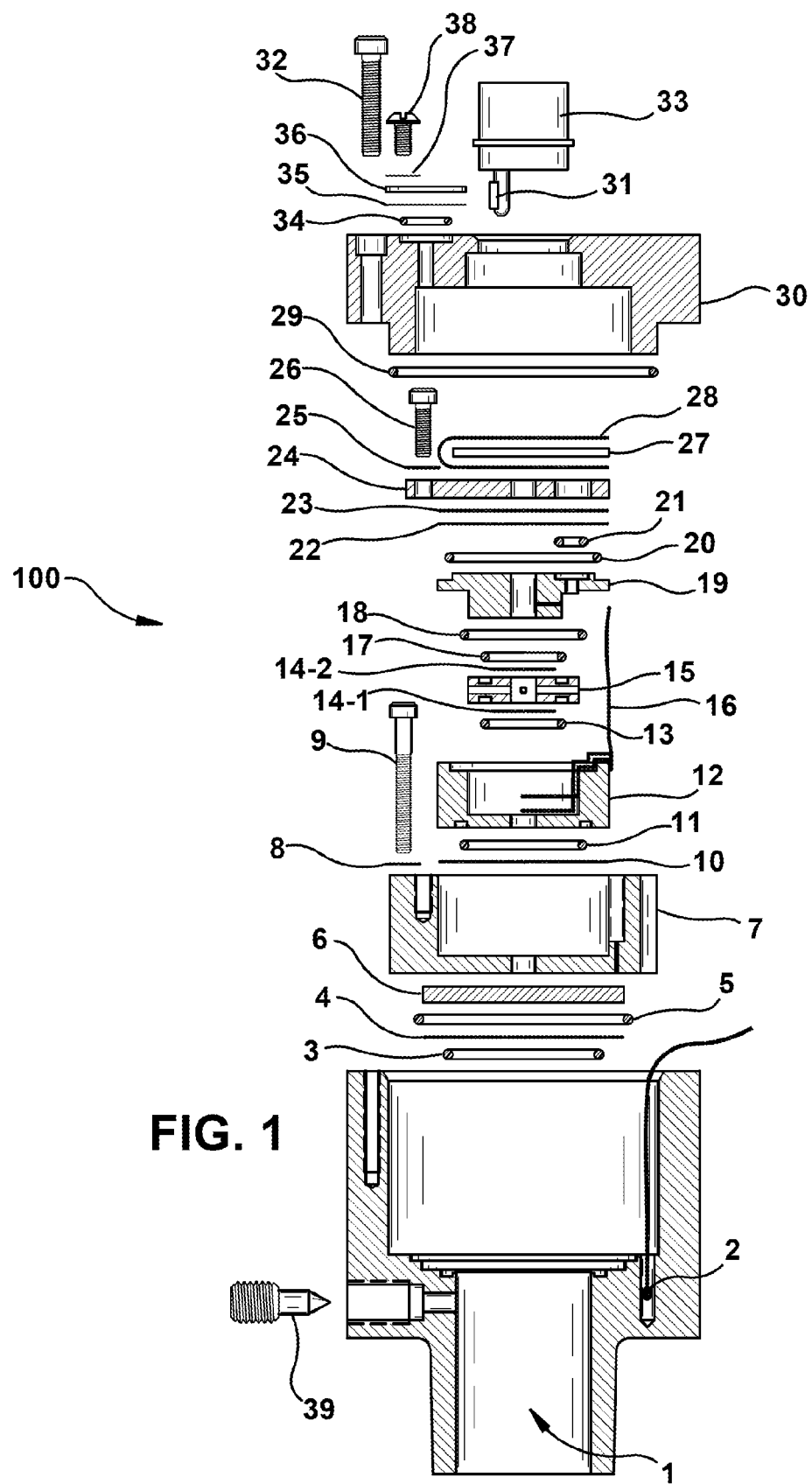
FIG. 1 is an exploded, cross-sectional illustration of an example fuel cell sensor assembly.

Various types of electrical equipment can experience electrically and/or thermally induced damage. Electrical equipment can include, but are not limited to, power transformers, reactors, auto transformers, instrument transformers, arc furnace transformers, rectifier transformers, distribution transformers, tap changers and oil-filled power cables. Power transformers, for example, operate continuously and are subject to extremes of temperature. The insulation used in transformers must be extremely durable and resistant to degradation. Typically, insulating oil and/or cellulosic insulation are used as the insulating mediums. The insulating oil and cellulosic insulation can break down and decompose into its constituent elements when subjected to electrical discharges or elevated temperatures.

The insulating oil used in transformers can begin to decompose when the temperature reaches 150 degrees C. Generally, hydrogen is generated by thermal decomposition. At the higher temperature levels acetylene can also be generated. Partial electrical discharges (i.e., corona) and low level arcing generate hydrogen and small amounts of acetylene. High level arcing generates acetylene and hydrogen.

The presence of acetylene and hydrogen, and other gases, can be indicative of the overall health and condition of the transformer. Early detection of rising levels of specific gases or constituents can be used to correct for failing insulation or component malfunction. When levels of hydrogen are more than about 100 ppm and/or acetylene are more than about 35 ppm in the insulating oil, the equipment in question should be monitored closely. If the levels of hydrogen and/or acetylene approach or exceed these levels, a faulty component or other failure could be indicated. Accordingly, it would be very desirable to detect these conditions early and service any equipment before a catastrophic failure occurs.

In accordance with aspects of the present invention, a fuel cell sensor is provided that can simultaneously detect multiple gases in a fluid (e.g., a dielectric fluid). In some embodiments of the invention, acetylene and hydrogen are detected. However, the invention also contemplates detecting other gases and two or more different gases simultaneously. In one embodiment, the fuel cell sensor comprises one or more electrodes for detecting acetylene and one or more electrodes for detecting hydrogen. In other aspects one electrode can be segmented into two or more sections, where one section can be configured to detect acetylene and the other section can be configured to detect hydrogen. In additional aspects, the ratio between the area of the two sections (i.e., the acetylene detecting section and the hydrogen detecting section) can be adjusted for specific applications. For example, the ratio of the area of the two sections could range from about 1:1 (i.e., each section of equal area) to about 5:1 (i.e., the acetylene detecting area is five times greater than the hydrogen detecting area). The sensor can be configured to have a greater area for the acetylene detecting electrode or a greater area for the hydrogen detecting electrode.

The various embodiments of the present invention, described herein, provide a sensor instrument that can be used as an early warning device that can alert operations and maintenance personnel to developing fault conditions that could lead to equipment failures and unscheduled outages. The outputs of the sensor can be used to warn personnel when diagnostic or remedial actions are needed.

FIG. 1 illustrates a detailed, exploded view of one embodiment of a fuel cell sensor 100 for measuring acetylene and hydrogen in fluids, according to the present invention. The sensor 100 includes a cavity 1 for facilitating diffusion of acetylene and hydrogen from an external fluid. A thermistor 2 can be housed within the base portion to sense the temperature of the probe body. A plurality of O-rings 3, 5, 11, 13, 17, 18, 20. 29 and 34 seal off the internal components of the sensor. A membrane 4 can be placed between O-rings 3 and 5 to prevent the fluid from entering into the central portion of the sensor 100. The membrane 4 permits the diffusion of selected gases (e.g., acetylene and hydrogen) but prevents the fluid (e.g., dielectric oil used in a transformer) from passing therethrough. Teflon® is one example of any suitable membrane that could be used for membrane 4. In one specific embodiment, the membrane 4 could be a Teflon® membrane 1 mil in thickness (1 mil=1/1000 of an inch). Any membrane capable of passing selected gases (e.g., acetylene and hydrogen) and preventing the passage of the target fluid (e.g., dielectric oil) would suffice. A porous support disk 6 can be placed next to the membrane 4 to provide rigidity to the membrane 4. The porous support disk could be any rigid material that will allow the selected gases to pass therethrough (e.g., stainless steel or any porous support of appropriate material).

A fuel cell cup 7 receives the fuel cell detection assembly, and is secured to the base portion via washer 8 and bolt 9. A membrane 10 can be placed at the bottom of the cup 7. The membrane can be comprised of a GORE-TEX® (a registered trademark of W.L. Gore & Associates) material or other suitable membrane. An O-ring 11 can be used to seal the bottom of the fuel cell body 12 to the fuel cell cup 7. A pair of electrodes 14-1 and 14-2 are placed on opposite ends of a fuel cell spacer 15. The fuel cell spacer 15 includes a central cavity filled with an acid gel electrolyte. The central cavity passes from electrode 14-1 to electrode 14-2. A fuel cell cover 19 can be attached to fuel cell body 12 with any suitable fastener.

Additional membranes 22 and 23 can be placed above the fuel cell cover 19. In one embodiment the membrane 22 could be a Teflon® (a registered trademark of DuPont) material of about 2 mils in thickness, and the membrane 23 could be a GORE-TEX® material of about 7 mils in thickness. A fuel cell cover plate 24 can be secured to the fuel cell cup 7 by the use of appropriate fasteners (e.g., washer 25 and bolt 26). A salt bag 27 can be used to maintain a substantially constant moisture level (e.g., about 20%) inside the senor. The salt bag 27 can be partially or completely enveloped by a membrane 28. In one embodiment, membrane 28 could be comprised of a GORE-TEX® material.

The probe cap 30 can be secured to the base portion with bolt 32 or any other suitable fastening means. A load resistor 31 is connected to connector 33, and is used to obtain the voltages between electrodes 14-1 and 14-2. A ventilation membrane 35 and vent cover 36 are secured to the probe cap with the use of washer 37 and screw 38. The ventilation membrane allows ambient air (including oxygen) to enter the probe body and reach common electrode 14-2. Bleed screw 39 can be used to take physical samples of the fluid being monitored.

Figure 2:
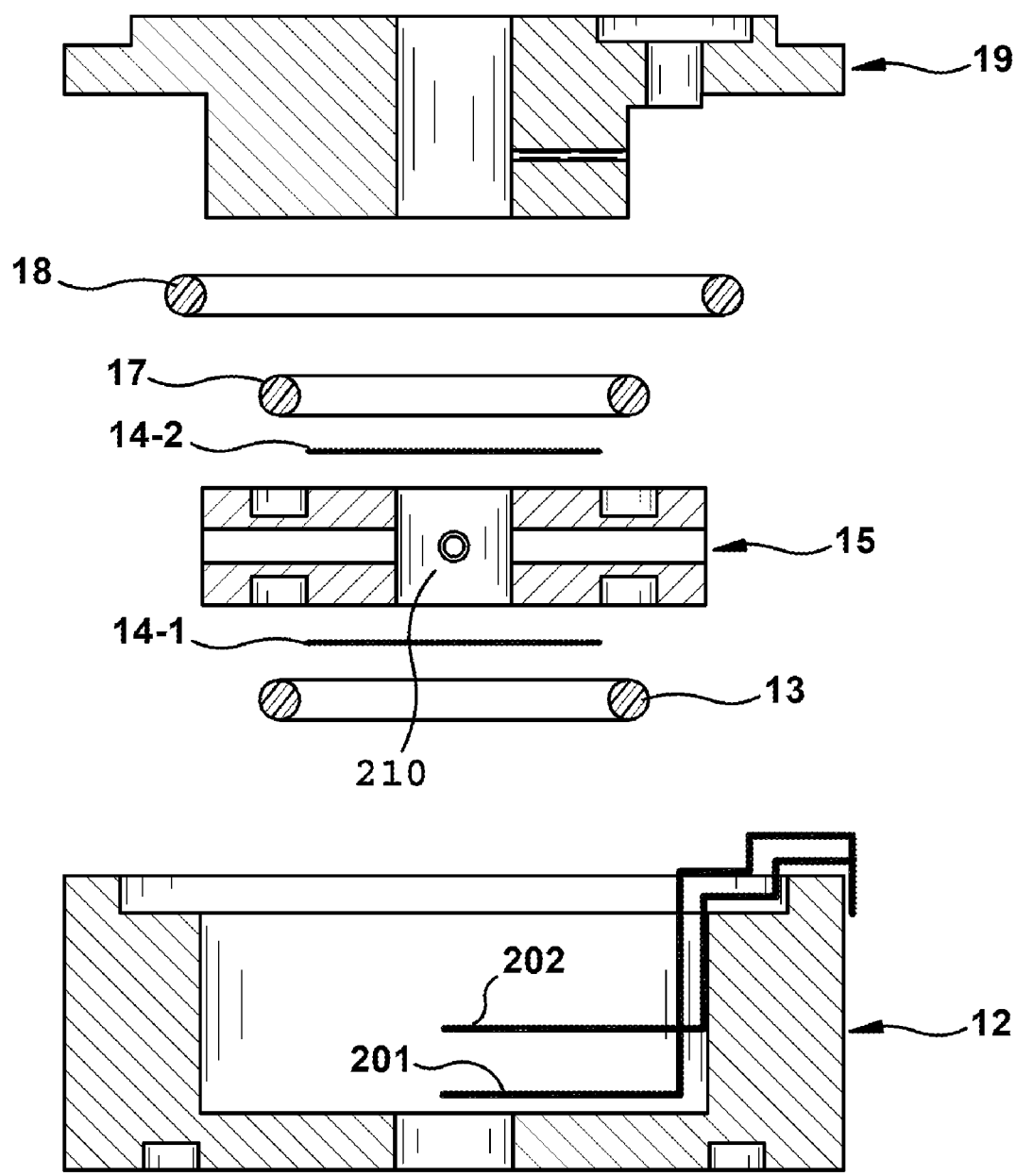
FIG. 2 is an enlarged, cross-sectional illustration of a fuel cell and fuel cell cover assembly.

FIG. 2 shows an enlarged view of one embodiment of the fuel cell sensor. Spacer 15 includes an acidic electrolyte 210 contained in a central cavity. The common electrode 14-2 is placed at one end of the cavity and the sensing electrode 14-1 is placed at the opposite end of the cavity in spacer 15. Electrical contact is made to electrodes 14-1 and 14-2 via a plurality of lead wires. Lead wire 201 can be connected to sensing electrode 14-1 and lead wire 202 can be connected to common electrode 14-1. In some embodiments lead wire 14-1 may comprise a plurality of leads, where each lead is connected to a different portion of electrode 14-1. Output of the sensor 100 is measured between the sensor leads 14-1 and 14-2 through a resistor 31 and connector 33 as illustrated in FIG. 1.

Figure 3:
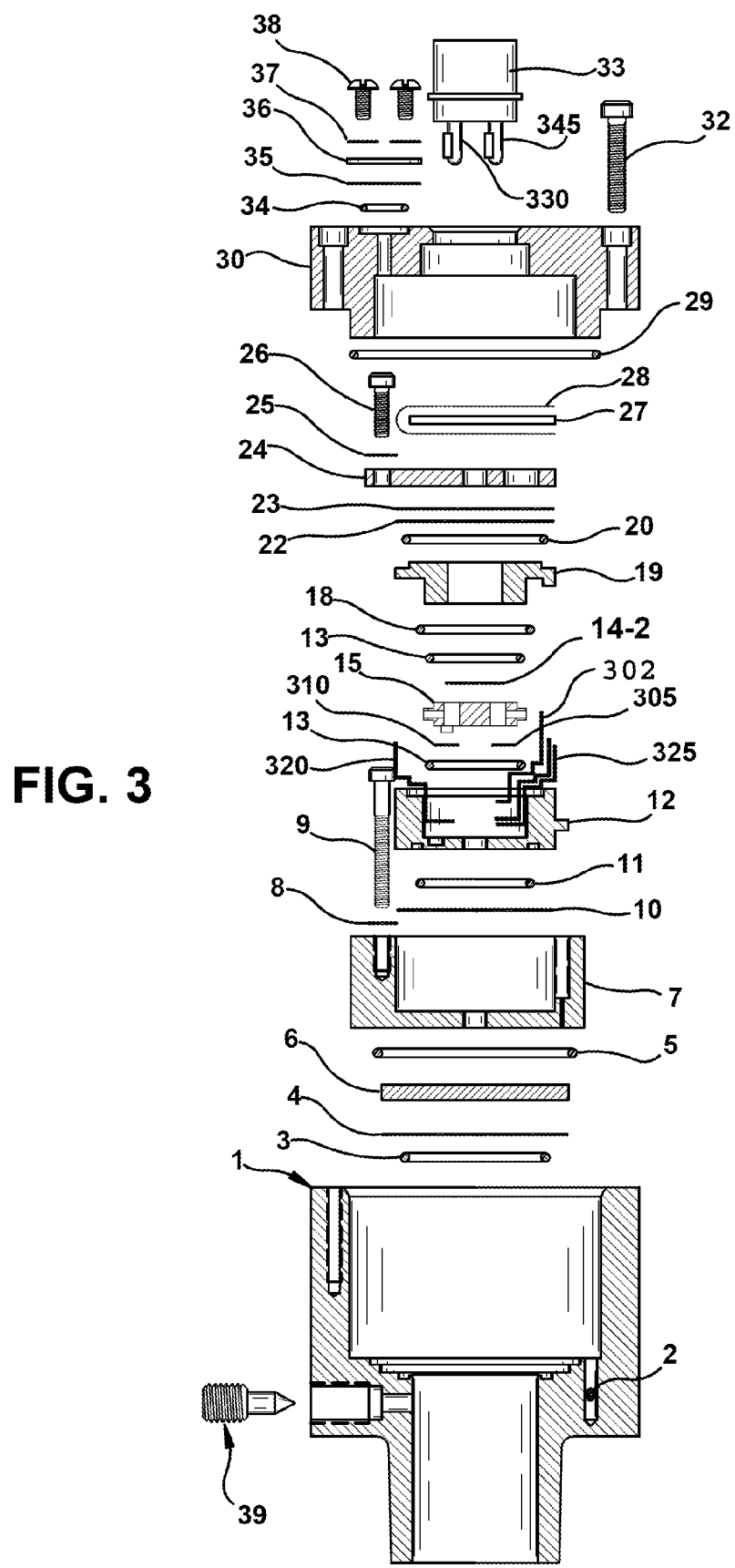
FIG. 3 is an exploded, cross-sectional illustration of another embodiment of a fuel cell sensor.

FIG. 3 illustrates another embodiment of the present invention, with like elements indicated by the same numerals as in FIGS. 1-2. In this embodiment, sensing electrode is comprised of a plurality of distinct sensing electrodes 305 and 310. For example, electrode 305 could be an acetylene detecting electrode and electrode 310 could be a hydrogen detecting electrode. Even though only one electrode of each type is indicated, there could be multiple electrodes 305 for sensing acetylene, and/or multiple electrodes 310 for sensing hydrogen. A wire lead 302 can be used for connecting to the common electrode 14-1. Wire lead 320 can be used to connect to acetylene detecting electrode 310, and wire lead 325 can be used to connect to hydrogen detecting electrode 305. The wire leads in contact with the electrodes can be made of noble metals (e.g., platinum or gold). The noble metal leads can then be soldered to another wire lead which can be formed of any suitable metal, including but not limited to, copper, aluminum, etc.

In this embodiment, two load resistors (which may have different resistances) can be connected to the sensing electrodes. Resistor 330 can be connected to the acetylene detecting electrode 310 via lead 302. Resistor 345 can be connected to the hydrogen detecting electrode 305 via lead 325. In one embodiment, resistor 330) can be a fixed load resistance of 2200 ohms, and resistor 345 can be a fixed load resistance of 500 ohms.

Figure 4:
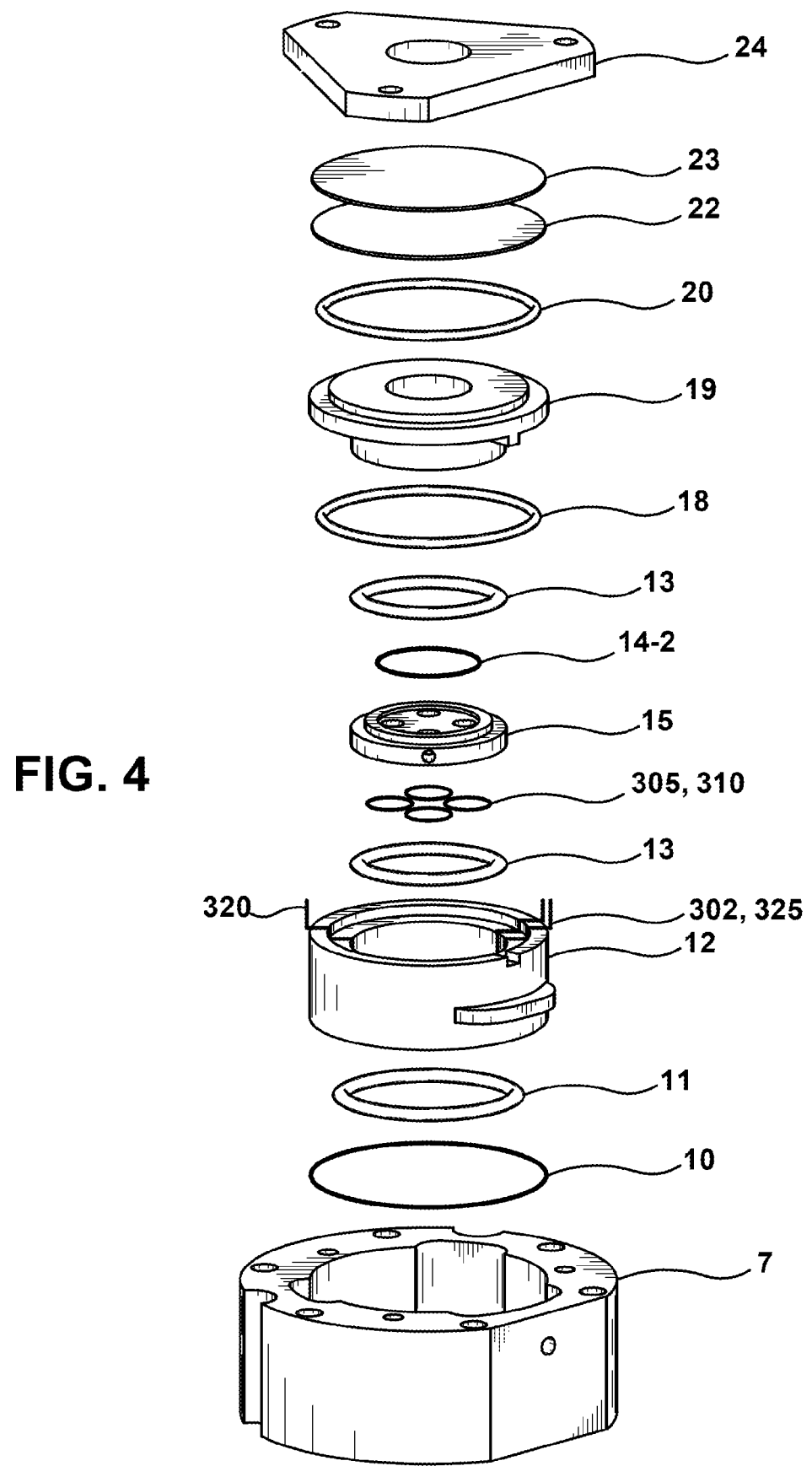
FIG. 4 is an exploded, cross-sectional illustration of another embodiment of the fuel cell sensor.

FIG. 4 illustrates an exploded, perspective view of elements 7 to 24 of FIG. 3. Sensing electrodes 305, 310 are shown to comprise four sensing electrodes in this view. For example, in this embodiment, one could employ one to three acetylene sensing electrodes 310, and one to three hydrogen detecting electrodes 310. The variation on the number and surface area of the multiple sensing electrodes are described in more detail hereafter.

Figure 5:
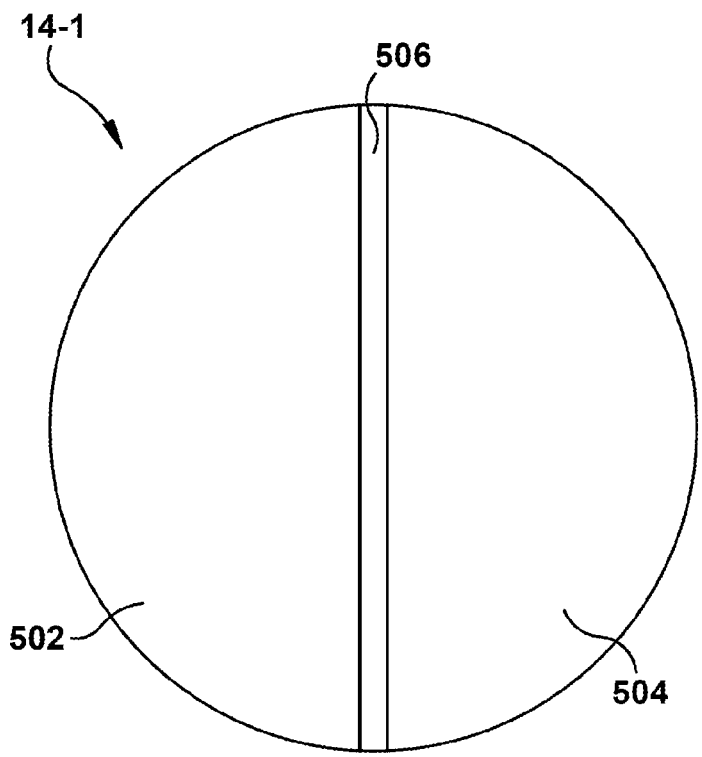
FIG. 5 is a top plan illustration of one embodiment of the first sensing means.

In one embodiment, and referring to FIG. 5, the sensing electrode 14-1 can comprise a multi-sectioned electrode, with each section responsive to a different constituent (e.g., acetylene or hydrogen). An acetylene responsive section 502 and a hydrogen responsive section 504 are both arranged on electrode 14-1. An adhesive 506 electrically insulates and bonds the two sections. The adhesive 506 is preferably a silicon, acid resistant adhesive, and one such adhesive is the Dow Corning® (a registered trademark of Dow Corning Corporation) 3145 adhesive/sealant. The electrodes 502 and 504 are shown located generally next to each other, but the layout of the electrodes 502 and 504 could take any form. For example, electrode 502 could be placed around electrode 504, where electrode 504 generally comprises a circular shape and electrode 502 generally comprises a "doughnut" like shape. The interface between the two electrodes 502 and 504 could be a jagged edge, an arcuate edge or a stepped edge, in addition to a linear edge as shown in FIG. 5.

The acetylene detecting electrode portion 502 can be comprised of gold, i.e. a gold electrode means. In accordance with the present invention the acetylene detecting electrode portion 502 (e.g. a gold electrode) may have an electro-catalytic activity for favoring the oxidation of acetylene as against the oxidation of gases like hydrogen, carbon monoxide, ethylene, methane, ethane and the like. The specificity of a gold electrode means for the electrochemical oxidation of acetylene may be enhanced by using modified electrode structures. In accordance with the present invention the acetylene detecting electrode portion 502 may for example comprise or consist of a gas porous gold film or layer interfacing a solid ion conducting substrate or ion exchange membrane, i.e. such that the electrode has a gold/substrate interface zone wherein gold is dispersed within the matrix of the substrate (e.g. at least adjacent the surface boundary of the substrate. The solid ion conducting/exchange membrane may be for example a perfluorosulfonic acid film, a perfluorosulfonic acid/PTFE copolymer film, the above mentioned Nafion® membrane(s) available from DuPont, or any other suitable ion exchange film.

The hydrogen detecting electrode 504 may be any other electrode means having electro-catalytic activity for the reduction of hydrogen. The hydrogen detecting electrode 504 may be a noble metal electrode; for example, a platinum electrode or a platinum-carbon electrode, or at least one noble metal/carbon combination and a polymeric hydrophobic binder. The hydrogen detecting electrode 504 may also comprise a platinum-carbon layer adhered to a graphite layer (e.g., a graphite paper). The common electrode 14-2 can be configured of the same materials as the hydrogen detecting electrode 504.

The electrode 14-1 as shown in FIG. 5 has a ratio between the area of the acetylene electrode 502 and the hydrogen electrode 504 of about 1:1. However, this ratio can be changed or adjusted to increase the electrode's sensitivity to specific gases or constituents.

Figure 6:
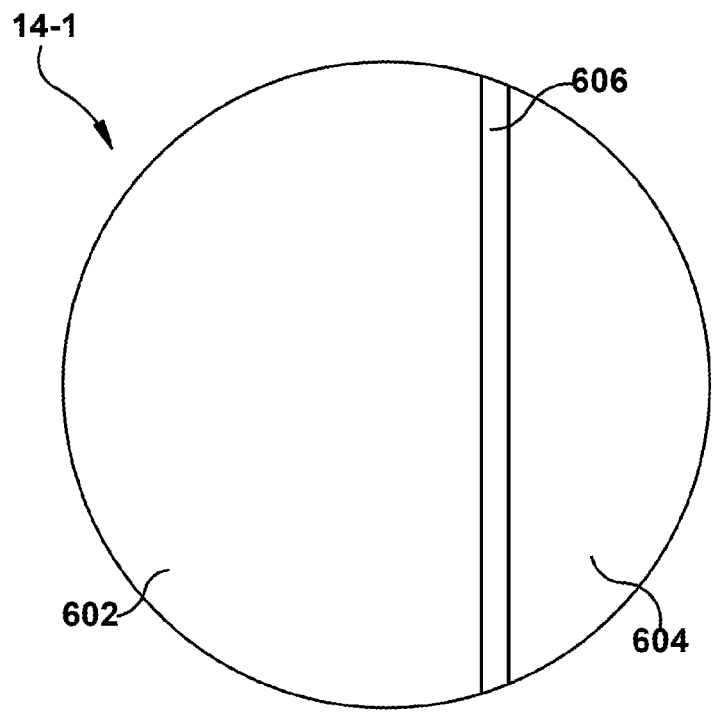
FIG. 6 is a top plan illustration of another embodiment of the first sensing means.

FIG. 6 shows an electrode 14-1 having a ratio of about 3:1 for the area between the acetylene electrode 602 and the hydrogen electrode 604. The adhesive portion is indicated by 606. The ratio of the area of the acetylene electrode to the area of the hydrogen electrode can range between about 10:1 to about 1:10, or other ratios as the specific application may require. When the two gases to be detected are acetylene and hydrogen, a preferred range is about 1:1 to about 5:1 for the acetylene/hydrogen electrode surface area ratio.

Figure 7:
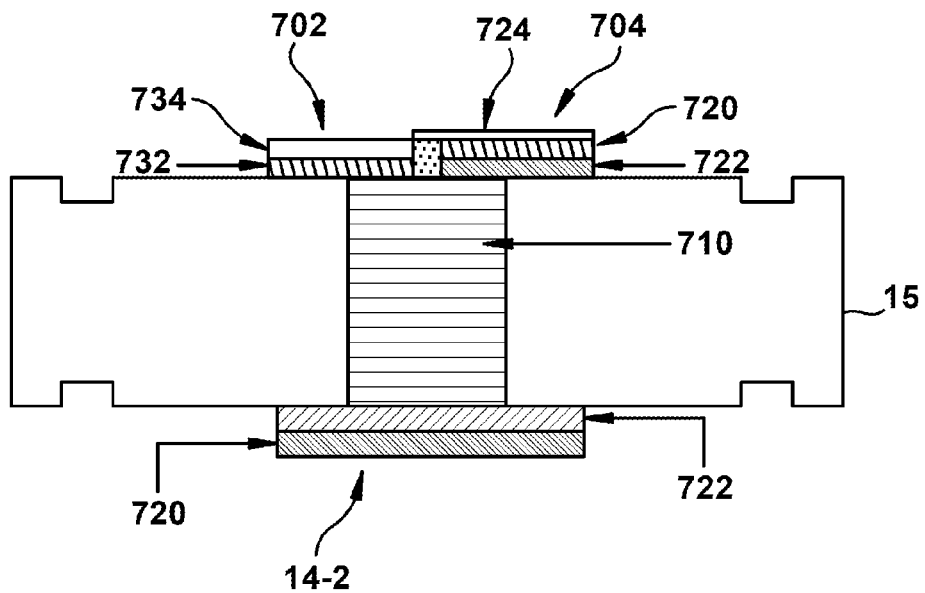
FIG. 7 is a cross-sectional illustration of the sensor according to one embodiment of the present invention.

FIG. 7 shows a cross-sectional view of a portion of one embodiment of the fuel cell sensor. The fuel cell spacer 15 has a central via filled with an acid gel electrolyte 710. The common electrode 14-2 is comprised of a graphite paper layer 720 and a Pt—C (platinum-carbon) layer 722. Similarly, the hydrogen detecting electrode 704 portion is also comprised of a graphite paper layer 720 and a Pt—C (platinum-carbon) layer 722. The hydrogen detecting electrode 704 also can include a Teflon® overlayer 724. The acetylene detecting electrode 702 is comprised of a Nafion® membrane layer 732 and a gold layer 734. An electrically insulating adhesive 740 bonds the acetylene detecting electrode and the hydrogen detecting electrode together, and one such adhesive is the Dow Corning® 3145 adhesive/sealant.

The acidic electrolyte 710 used is to be of such a composition so as to enable the occurrence of the reaction of electrochemical oxidation of the acetylene at the acetylene electrode 702 and hydrogen at the hydrogen electrode 704 and that of reduction of oxygen at the common electrode 14-2 (located at the bottom of FIG. 7); in general the electrolyte is acidic. For that purpose, any type of acidic electrolyte respecting the electrochemical operation principle of the detector in accordance with the present invention may be used. Thus the oxido-reduction reaction can be initiated by means of an electrolyte constituted by an acid, such as phosphoric acid, sulfuric acid or perchloric acid. The electrolyte may be a gel electrolyte, i.e. an electrolyte gelled by a conventional gelling agent(s) such as Cab-O-Sil® (registered trademark of the Cabot Corp.) fumed silica. It may, for example, be a gel electrolyte comprising sulfuric acid. On the other hand, the electrolyte may be a solid acidic proton conductor electrolyte, which may for example be a solid polymeric electrolyte; the electrolyte may in particular be a solid ion conducting substrate such as for example a perfluorosulfonic acid polymers. One type of such solid electrolytes are the Nafion® Perfluorosulfonic acid polymers. Hereinafter, these types of membranes or substrates will unless otherwise indicated be referred to simply as Nafion®. Other proton conducting membranes or substrates may for example be obtained from Dow Corning®. The acidic electrolyte may also be comprised of sulfuric acid ($H_2SO_4$), fumed silica ($SiO_2$) and water ($H_2O$).

Figure 8:
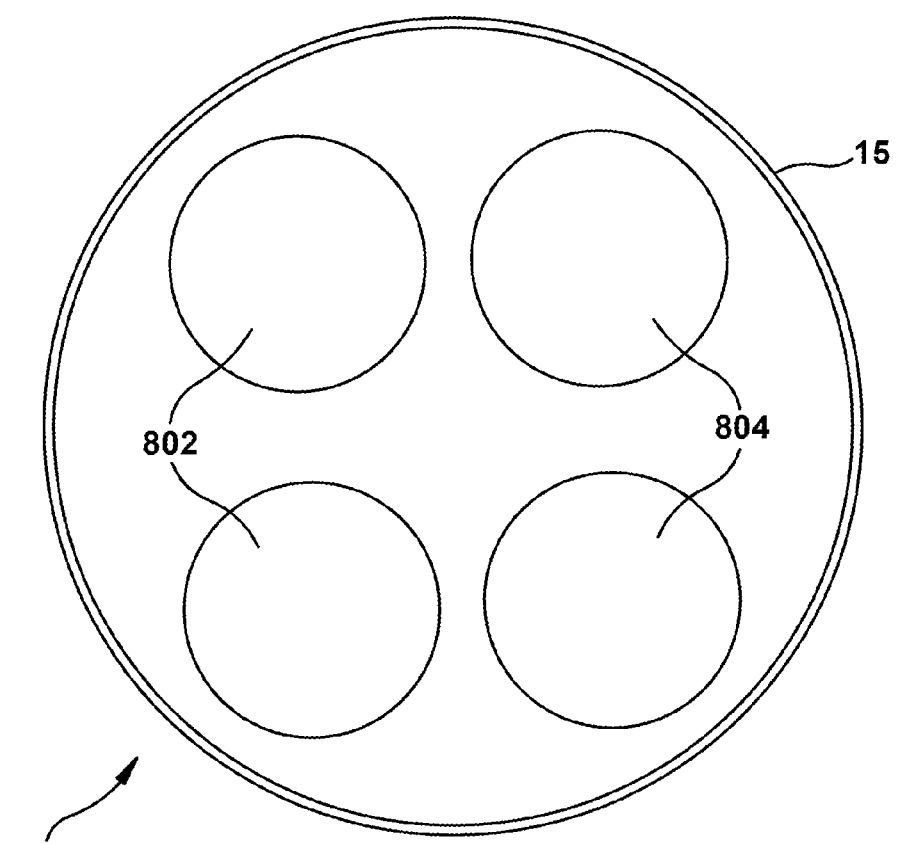
FIG. 8 is a top plan illustration of another embodiment of the first sensing means.

FIG. 8 shows a top, plan view of another embodiment of the present invention. The acetylene and hydrogen detecting electrodes can be comprised of multiple electrodes housed within a single device. In this embodiment, and as one example only, the sensor 100 can include two acetylene detecting electrodes 802 and two hydrogen detecting electrodes 804. The electrodes 802, 804 can be disposed over four individual cavities filled with an acid gel electrolyte. One common electrode can be arranged on the opposite side of the electrolyte filled cavities. The use of four electrodes are for example only, and any number of acetylene and/or hydrogen detecting electrodes could be arranged within sensor 100.

Figure 9:
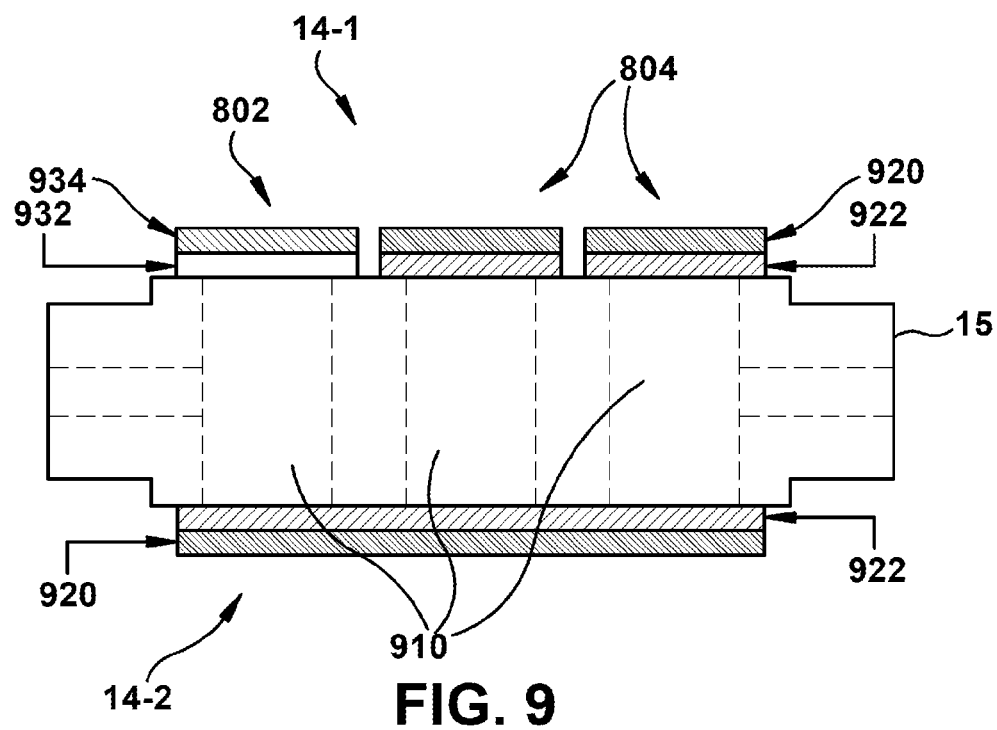
FIG. 9 is a cross-sectional illustration of the sensor shown in FIG. 8.

FIG. 9 illustrates an angled, side view of the sensor of FIG. 8. One acetylene electrode 802 and two hydrogen electrodes 804 can be seen on top of spacer 15. In this view, three cavities can be seen and are shown in phantom, and these cavities are filled with an acid gel electrolyte 910. The common electrode 14-2 is comprised of a graphite paper layer 920 and a platinum-carbon layer 922. The common electrode 14-2 spans all four cavities under electrodes 802 and 804. The hydrogen detecting electrodes 804 are comprised of a graphite paper layer 920 and a platinum-carbon layer 922. The acetylene detecting electrodes 802 are comprised of a Nafion® membrane 932 and a gold layer 934.

Figure 10:
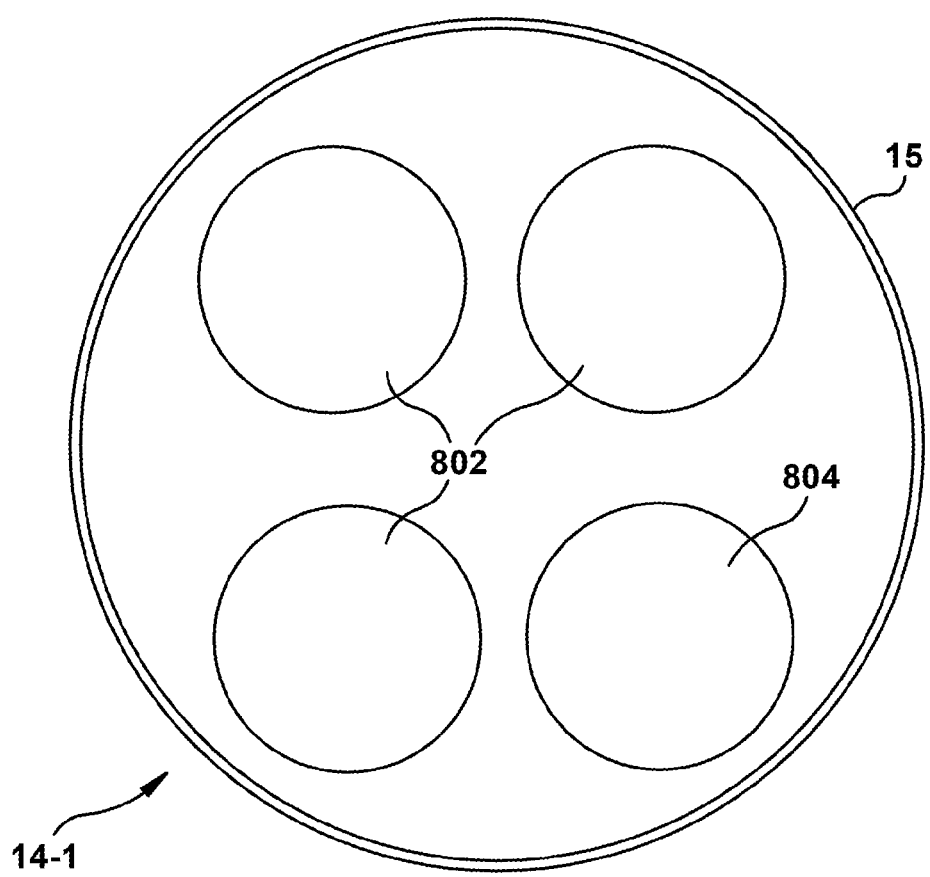
FIG. 10 is a top plan illustration of another embodiment of the first sensing means.

FIG. 10 illustrates a top plan view of another embodiment of the present invention. In this embodiment, three acetylene detecting electrodes 802 are arranged on spacer 15 with one hydrogen detecting electrode 804. The three acetylene detecting electrodes will increase the sensitivity of the device to acetylene while reducing or maintaining the sensitivity to hydrogen. This embodiment has a surface area ratio of acetylene to hydrogen detecting electrodes of 3:1.

The acetylene and hydrogen detecting electrodes can be connected to the common electrode through a suitable fixed load resistance (e.g., 500 to 2200 ohms). In one embodiment, a fixed load resistance of 2200 ohms can be connected to the acetylene detecting electrode(s), and a fixed load resistance of 500 ohms can be connected to the hydrogen detecting electrode(s). Any suitable electronic signal measuring means can be attached across the load resistances so as to be able to permit the measuring of the voltages generated by the oxido-reduction reactions occurring between (1) the acetylene detection electrodes and the common electrode, and (2) the hydrogen detection electrode(s) and the common electrode. The electronic signal measuring means can be connected to any suitable display means to provide a visual reading with respect to the concentrations of acetylene and hydrogen. The signals generated by the fuel cell is essentially a current having an intensity proportional to the acetylene content and the hydrogen content in the fluid of interest.

The sensor device 100 can be used for the simultaneous detection of both acetylene and hydrogen gas in a fluid (e.g., a transformer's dielectric oil). The sensor can also detect the respective proportions (even if they are different) of each gas. The separate signal measured between the acetylene sensing electrode and the common electrode is proportional with the concentration of acetylene in the fluid to be analyzed. The separate signal measured between the hydrogen sensing electrode and the common electrode is proportional with the concentration of hydrogen in the fluid to be analyzed. As described previously, the sensitivity of the sensor can be made more sensitive to acetylene by increasing the surface area of the acetylene detecting electrode(s) in relation to the surface area of the hydrogen detecting electrode(s). Conversely, the sensitivity of the sensor can be made more sensitive to hydrogen by increasing the surface area of the hydrogen detecting electrode(s) in relation to the surface area of the acetylene detecting electrode(s).

The sensor device 100 was described primarily with reference to detecting acetylene and hydrogen. However, the sensor device could be used to detect other gases or fluid constituents as well. In addition, one, two, three or more gases could be detected by the use of suitable electrodes housed within a single sensor device. Other constituents or gases, including but not limited to, hydrogen ($H_2$), carbon monoxide (CO), methane ($CH_4$), ethane ($C_2H_6$), ethylene ($C_2H_4$), and acetylene ($C_2H_2$) can be detected and measured with the sensor herein described.

While the invention has been described in terms of various specific embodiments, those skilled in the art will recognize that the invention can be practiced with modification within the spirit and scope of the claims.

What is claimed is:

1. A fuel cell sensor for detecting the presence of at least one of acetylene and hydrogen in a fluid, comprising:
   a sensing element comprising first and second gas diffusing electrodes spaced from one another, said first gas diffusing electrode for sensing acetylene, the first gas diffusing electrode having a first area and said second gas diffusing electrode for sensing hydrogen, the second gas diffusing electrode having a second area;
a common electrode;
a fuel cell spacer having an acidic electrolyte disposed between said sensing element and said common electrode;
wherein, said sensing element is configured so that the first area of the first gas diffusing electrode is different than the second area of the second gas diffusing electrode.

2. The fuel cell sensor of claim 1, wherein a specific ratio of the first area in relation to the second area is between 1:1 to about 5:1.

3. The fuel cell sensor of claim 1, wherein a specific ratio of the first area in relation to the second area is between about 1:10 to about 10:1.

4. The fuel cell sensor of claim 1, wherein:
said first gas diffusing electrode comprises a gas porous gold film and an ion exchange membrane; and
said second gas diffusing electrode and said common electrode comprise a graphite layer and a platinum-carbon layer.

5. The fuel cell sensor of claim 1 wherein said first and second gas diffusing electrodes are spaced from one another by an insulating adhesive.

6. The fuel cell sensor of claim 1 further comprising:
a gas permeable membrane located between said fluid and said sensing element, said gas permeable membrane comprises a fluoropolymer film and a porous support.

7. The fuel cell sensor of claim 1, wherein said acidic electrolyte comprises, at least one of, sulfuric acid (H2SO4), fumed silica (SiO2), and water (H2O).

8. The fuel cell sensor of claim 1, wherein said fuel cell spacer comprises polypropylene.

9. A fuel cell sensor for detecting the presence of acetylene and hydrogen in a fluid, comprising:
at least one first sensing element for sensing acetylene;
at least one second sensing element for sensing hydrogen;
a common electrode;
a fuel cell spacer having an acidic electrolyte disposed between both said first and second sensing elements and said common electrode.

10. The fuel cell sensor of claim 9, wherein:
said first sensing element comprises a gas porous gold film and an ion exchange membrane; and
said second sensing element and said common electrode comprise a graphite layer and a platinum-carbon layer.

11. The fuel cell sensor of claim 9, comprising:
two first sensing elements; and
two second sensing elements.

12. The fuel cell sensor of claim 9, comprising:
three first sensing elements; and
one second sensing element.

13. The fuel cell sensor of claim 9, further comprising:
a gas permeable membrane located between said fluid and said at least one first sensing element and said at least one second sensing element, and said gas permeable membrane comprises a fluoropolymer film and a porous metallic support disk.

14. The fuel cell sensor of claim 9, wherein said acidic electrolyte comprises a mixture of sulfuric acid (H2SO4), fumed silica (SiO2) and water (H2O).

15. The fuel cell sensor of claim 9, wherein said fuel cell spacer comprises polypropylene.

16. An electrochemical sensing element comprising:
at least one first electrode sensitive to acetylene;
at least one second electrode sensitive to hydrogen;
a common electrode;
wherein said electrochemical sensing element can be used for the simultaneous measurement or quantification of acetylene and hydrogen dissolved in a fluid, and wherein a surface ratio between the at least one first electrode and the at least one second electrode is about 2:1 to about 4:1.

17. The electrochemical sensing element of claim 16, wherein said at least one first electrode and said at least one second electrode can detect acetylene gas or hydrogen gas in different proportions.

18. The electrochemical sensing element of claim 16, wherein:
a first signal measured between said at least one first electrode and said common electrode is proportional with the concentration of acetylene in said fluid; and
a second signal measured between said at least one second electrode and said common electrode is proportional with the concentration of hydrogen in said fluid.

* * * * *